Figure 1:
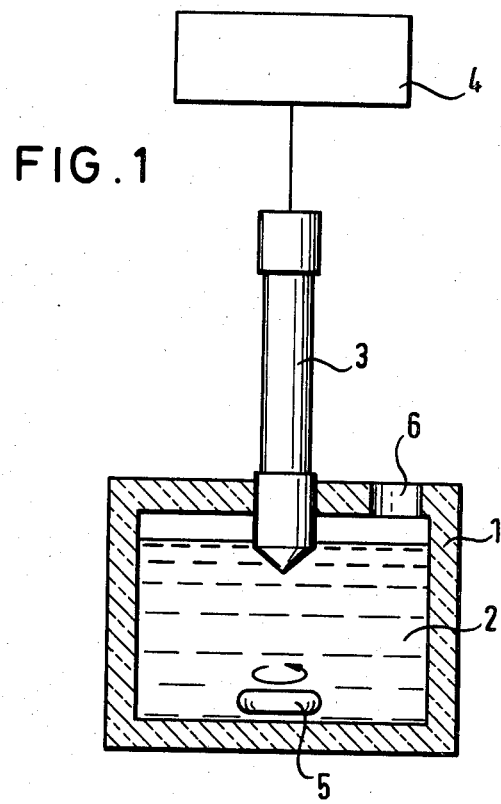

United States Patent [19]

Gauhl et al.

[11] 4,399,218

[45] Aug. 16, 1983

[54] METHOD AND REAGENT FOR THE DETERMINATION OF GLYCERIN

[75] Inventors: Helmgard Gauhl; Hans Seidel; Gunter Lang, all of Tutzing; Albert Röder, Seeshaupt; Joachim Ziegenhorn, Starnberg, all of Fed. Rep. of Germany

[73] Assignee: Boehringer Mannheim GmbH, Mannheim-Walhof, Fed. Rep. of Germany

[21] Appl. No.: 228,010

[22] Filed: Jan. 23, 1981

[30] Foreign Application Priority Data

Feb. 5, 1980 [DE] Fed. Rep. of Germany ....... 3004129

[51] Int. Cl.$^3$ .......................... C12Q 1/26; C12Q 1/28; C12Q 1/30; C12Q 1/44; C12N 1/14; C12N 9/04; C12R 1/66

[52] U.S. Cl. ......................................... 435/25; 435/19; 435/27; 435/28; 435/190; 435/254; 435/805; 435/810; 435/815; 435/913; 435/816

[58] Field of Search ..................... 435/25, 27, 815, 28, 435/19, 816, 190, 254, 913, 814, 805, 810

[56] References Cited

U.S. PATENT DOCUMENTS

| | | | |
|---|---|---|---|
| 4,098,574 | 7/1978 | Dappen | 435/28 |
| 4,202,941 | 5/1980 | Terada et al. | 435/25 |
| 4,212,938 | 7/1980 | Gruber et al. | 435/19 |
| 4,223,090 | 9/1980 | Mazza | 435/25 |
| 4,255,519 | 3/1981 | Terada et al. | 435/25 |
| 4,266,023 | 5/1981 | Terada et al. | 435/25 |

*Primary Examiner*—Esther M. Kepplinger
*Attorney, Agent, or Firm*—Felfe & Lynch

[57] ABSTRACT

For the determination of glycerin by oxidation with oxygen in the presence of glycerinoxidase and measurement of the oxygen consumption or of the $H_2O_2$ formation, a glycerinoxidase from Aspergillus spec. DSM 1729 is used. A reagent suitable for this method consists of glycerinoxidase from Aspergillus spec. DSM 1729 and a system for the determination of $H_2O_2$ and contains additionally, if desired, an agent for the saponification of esterified glycerin.

16 Claims, 2 Drawing Figures

METHOD AND REAGENT FOR THE DETERMINATION OF GLYCERIN

The invention relates to a method and a reagent for the enzymatic determination of glycerin by means of a specific glycerinoxidase, the latter itself, and its production.

The determination of triglycerides (=glycerin esters of long-chain fatty acids) is of considerable importance in medical diagnosis. An elevated triglyceride level in the blood is an important risk factor in arteriosclerosis. At high triglyceride levels, that is, hypertriglyceridemia, coronary insufficiency and coronary infarction occur more frequently than at low triglyceride levels. Hypertriglyceridemia promotes the occurrence of arteriosclerosis and coronary diseases, and therefore it must be recognized early so that treatment can be started in a timely manner. A quick and reliably performable method for the determination of triglycerides or glycerin is therefore of great importance.

The known and usable methods for triglyceride determination are based on the enzymatic hydrolysis of the triglycerides by means of lipase/esterase and determination of the released glycerin, for example by means of glycerokinase-pyruvatekinase-lactatedehydrogenase, or by means of glycerinoxidase (DE-AS No. 2,817,087).

These known methods, however, have substantial disadvantages. Thus, in the glycerokinase method the stability of the reagent is poor on account of the presence of numerous sensitive coenzymes and enzymes, and blank value tests must always be performed. In the known glycerinoxidase method, an important disadvantage is that the enzyme is present in very small amounts in the known microorganisms which contain them and furthermore it has a low specific activity on the order of 30 units per milligram.

Therefore, the object of the invention is the creation of a new method and of a reagent for the determination of triglycerides and glycerin, which does not have the disadvantages of the formerly known glycerinoxidase method, yet retains its advantages.

This object is achieved according to the invention by a method for the determination of glycerin by oxidation with oxygen in the presence of glycerinoxidase and measurement of the oxygen consumption or of the formation of $H_2O_2$, which is characterized in that a glycerinoxidase from Aspergillus spec. DSM 1729 is used.

The invention is based on the surprising discovery of the microorganism Aspergillus spec. DSM 1729, which not only has a content of glycerinoxidase that is several powers of ten greater in comparison to known glycerinoxidase-containing microoganisms, but in addition contains a glycerinoxidase having a substantially higher specific activity.

In the process of the invention, the oxygen consumption or the $H_2O_2$ that is formed can be determined by methods known in themselves for this purpose. Preferably the oxygen consumption is determined polarographically by oxygen electrode, since this method is especially suitable for automatic performance. Particularly suited for this purpose are the methods described in DE-OS 2,130,340 and DE-OS 2,130,308 for the polarographic measurement of oxygen consumption in an aqueous medium. Another suitable method is gas chromatography.

The $H_2O_2$ that is formed can be determined not only by titrimetry, but also by potentiometric, polarographic and colorimetric as well as enzymatic methods. The enzymatic methods using catalase and peroxidase are preferred, since these are not only extremely specific and reliable, but also they can be combined quite simply with the main reaction with the formation of hydrogen peroxide. Determination by means of catalase in the presence of beta-diketones, such as acetyl acetone and methanol, or ethanol or methylene glycol, and also determination by means of peroxidase in the presence of one or more chromogens, have proven to be particularly suitable. In the determination by means of catalase, acetyl acetone and methanol, the latter is oxidized to formaldehyde which enters into a color reaction with acetyl acetone, which can be measured. In the determination by means of peroxidase, compounds are used as chromogens which can be determined photometrically after the reaction.

One example of a suitable chromogen is 2,2'-aminobenzothiazoline sulfonic acid. Another preferred example is the Trinder indicator system (Ann. Clin. Biochem. 6 (1969), 24–27), in which phenol is coupled oxidatively with 4-aminoantipyrine (4-AAP) in the presence of POD or under the action of $H_2O_2$ to form a dye. Instead of phenol, phenol derivatives, aniline derivatives, naphthol, naphthol derivatives, naphthylamine, naphthylamine derivatives, aminoquinolines, hydroxyquinolines, dihydroxyphenylacetic acid and similarly reacting substances can be used. Instead of 4-aminoantipyrine, 4-aminoantipyrine derivatives, phenylenediaminesulfonic acid, MBTH (methylbenzothiazolonehydrazone), S-MBTH (sulfonated methylbenzothiazolonehydrazone), MBTH and S-MBTH derivatives, as well as compounds which react in a similar manner can be used.

Also subject matter of the invention is a reagent for the determination of glycerin, which is characterized by consisting of glycerinoxidase from Aspergillus spec. DSM 1729 and a system for determining $H_2O_2$. Preferably this reagent additionally contains an agent for the saponification of esterified glycerin, especially esterase or a combination of lipase and esterase. Reagents suitable for this purpose are known to the person skilled in the art and do not need to be further described.

In a preferred embodiment, the reagent of the invention consists essentially of glycerinoxidase, catalase, acetyl acetone, methanol and buffer, individually or mixed. In another preferred embodiment, the reagent consists essentially of glycerinoxidase, peroxidase, at least one chromogen, and buffer, individually or mixed. Glycerinoxidase is to be understood here and hereinafter always as glycerinoxidase from Aspergillus spec. DSM 1729. The Trinder system is preferred as the color indicator system.

The above-mentioned preferred reagent combinations can contain, in addition to the above-described, obligatory components, conventional solvents, stabilizers and/or surface active substances. All these additional substances are known to the person skilled in the art and commonly used in systems for the detection of hydrogen peroxide. Substances buffering between pH 5 and pH 10, preferably pH 6 and pH 9, are suitable as buffers. Typical examples of suitable buffers are phosphate buffer, tris buffer, TRA buffer, acetate buffer, citrate buffer and HEPES buffer (N-2-hydroxyethyl-piperazine-N-ethanesulfonic acid).

Preferably, the above-mentioned reagent combinations contain their essential components in the following quantity ratios:

2 to 150 U/ml glycerinoxidase,
0.5 to 100 U/ml peroxidase,
0.05 to 20 mmol/l at least one chromogen, and
0.001 to 0.1 g/ml at least one surface active agent in buffer, pH 6 to 9.

If the reagent combination is to be used for the kinetic determination, the following quantity ratios are preferred:

100 to 250 KU/l glycerinoxidase,
5 to 50 KU/l peroxidase,
0.2 to 5 mmol/l chromogen and, if desired,
1 to 5 g/l at least one surface active agent, or a multiple thereof, and buffer pH 6.8 to 8.0.

The culture of the microorganism Aspergillus spec. DSM 1729 used for the production of the glycerinoxidase is performed by methods known in themselves, using a nutrient medium which contains glycerin, malt extract and yeast extract as essential components in addition to buffer, salts and trace elements. For the foreculture, a medium is preferably used containing 1 to 100 g/l glycerin, 1 to 50 g/l malt extract, 1 to 10 g/l yeast extract, 1 to 100 g/l cottonseed meal, plus 0.2 to 5 g/l $K_2HPO_4 \cdot 3H_2O$ (or an equivalent amount of another $K_2HPO_4$ preparation), 0.2 to 5 g/l $KNO_3$, 0.1 to 5 g/l $CaCO_3$, 0.1 to 1 g/l NaCl, 0.001 to 0.1 g/l $FeSO_4$ (measured as heptahydrate) and 0.1 to 5 g/l $MgSO_4$ (measured as heptahydrate).

For the main culture, it is preferred to use a medium containing 20 to 200 g/l glycerin, 5 to 100 g/l malt extract, 0.5 to 5 g/l yeast extract, 0.2 to 5 g/l dipotassium phosphate, 0.2 to 5 g/l $KNO_3$, 0.1 to 5 g/l $CaCO_3$, 0.1 to 1 g/l NaCl, 0.001 to 0.1 g/l ferrosulfate and 0.1 to 5 g/l magnesium sulfate. What is stated above regarding the foreculture applies accordingly to the individual salts.

The foreculture is best performed with rocking and aeration at temperatures between 25° and 40° C. The length of time is generally between 20 and 60 hours.

The same applies accordingly to the main culture as regards temperature and culture time. Particularly good results are achieved in the small fermenter with an input of 0.5 to 1 liter of air per minute per liter of medium.

Upon completion of the culture, the biomass is separated in the usual manner and the cells are disintegrated. The common methods can be used for disintegration, mechanical methods being preferred. The insoluble components are removed from the solution in which the cells were disintegrated, for example by centrifugation or suction filtering. The solution obtained can be used directly for the glycerin determination. Preferably, however, an additional purification of the enzyme is performed.

The purification can be performed by commonly known biochemical methods of enzyme fractionation. However, it has been found especially desirable to perform one procedure that is uncommon in enzyme factionation, namely a precipitation with tricloroacetic acid. The addition of trichloroacetic acid is commonly used only for the complete precipitation of proteins, that is, for the removal of albumin if only an albumin-free solution is desired. Surprisingly, however, it has been found that the enzyme of the invention can be precipitated by trichloroacetic acid without loss of activity and with a greater concentrating effect. The precipitation is best performed by the addition of trichloroacetic acid down to a pH in the range of 5.4 to 4.6. The desired enzyme is found in the separated precipitates, with a specific activity of approximately 300 U/mg.

If further purification is desired, it is best performed by acetone precipitation followed by ammonium sulfate fractionation and then treatment with a weakly basic ion exchange resin. In the acetone precipitation, it is desirable to add 0.25 to 0.35 volume of acetone to the solution. The ammonium sulfate fractionation is best performed at a molarity of 0.5 to 2.0. It results in a specific activity of more than 800 U/mg. Treatment with a weakly basic ion exchange resin, preferably with crosslinked dextran containing diethylaminoethanol groups (DEAE Sephadex) results in a three- to tenfold further purification and yields a glycerinoxidase having a specific activity of about 2500 to 8000 U/mg.

Since activities of 150,000 to 200,000 U/l of culture are achieved with the microorganism that is used in accordance with the invention, the amount of glycerin oxidase required for glycerin determination can be drastically reduced and the cost of production can be decidedly diminished.

The above-described method of culture and purification assumes that the enzyme does not go into the medium during the culture. By culture in the presence of detergents, however, at least part of the activity can be transferred to the medium. Also, extraction from the harvested cells with detergents is possible. The results, however, are inferior to those of mechanical disintegration, as for example in high pressure dispersion.

The enzyme of the invention is distinguished from the formerly known glycerinoxidases mainly by a substantially lower molecular weight. Whereas for example the glycerinoxidase forming glycerinaldehyde, which has formerly been used for glycerin determination, has a molecular weight of at least 300,000, the molecular weight of the enzyme of the invention amounts to only around 90,000. Furthermore, the activity of the enzyme of the invention is not inhibited by copper sulfate or lead acetate, while SH reagents inhibit it. In the case of the known glycerinoxidase mentioned above, however, SH reagents stabilize and copper sulfate and lead acetate inhibit their activity to an extent of about 90%. Additional important differences consist in a specific activity between 2000 and 8000 U/mg in the enzyme of the invention, compared with about 30 U/mg in the known enzyme. Also, the stability of the enzyme of the invention at pH values of 5.0 and 10.0 is substantially better, and the activity after 10 minutes at 37° C. still amounts under these conditions to 50 to 55% as compared to 6% and 3%, respectively, in the known enzyme.

The method and the reagent of the invention are suitable for the determination of glycerin and glycerin esters (triglycerides) in aqueous media of all kinds, such as food extracts, body fluids and especially serum. On the basis of the great specificity of the method, only free glycerin is determined. The determination of the esterified glycerin which is of primary interest can be performed after the latter has been saponified. The saponification is performed preferably enzymatically, since it can then be performed simultaneously with the actual glycerin determination.

The following examples will further explain the invention.

EXAMPLE 1

(1) Culture of the Microorganism 60 ml of a foreculture containing 10 g/l glycerin, 10 g/l malt extract, 5 g/l yeast extract, 10 g/l cottonseed meal, 1.5 g/l K$_2$PO$_4$.3H$_2$O, 1 g/l KNO$_3$, 2.0 g/l CaCO$_3$, 0.5 g/l NaCl, 0.01 g/l FeSO$_4$.7H$_2$O and 1.0 g/l MgSO$_4$.7H$_2$O, was inoculated with spores of Aspergillus spec. DSM 1729 and shaken and aerated for 48 hours at 30° C.

360 ml of the foreculture thus obtained was placed in 15 l of a main culture medium which contained 100 g/l glycerin, 40 g/l malt extract, 2.5 g/l yeast extract, 1.5 g/l K$_2$HPO$_4$.3H$_2$O, 1.0 g/l KNO$_3$, 2.0 g/l CaCO$_3$, 0.5 g/l NaCl, 0.01 g/l FeSO$_4$.7H$_2$O and 1.0 g/l MgSO$_4$.7H$_2$O and 1.0 g/l MgSO$_4$.7H$_2$O. In a 25 liter fermenter, which was stirred at 600 rpm and ventilated with 10 liters of air per minute, the main culture was then performed at 30° C. After 22 hours of culture, the activity amounted to 174,800 units per liter. The activity measurement was performed in 0.1 M TRA buffer, pH 8, at 25° C., with p-chlorophenol and 4-aminoantipyrine and 546 nm.

(2) Purification of the Enzyme 100 g of the dry mass obtained as described above is suspended in 5 l of 0.02 M acetate buffer, pH 6.0, and is disintegrated by high-pressure dispersion. Then it is centrifuged and the precipitate is discarded.

A 0.1x molar trichloroacetic acid solution is added to the supernatant fluid until a pH of 4.8 is reached. The precipitate is removed by centrifugation. It has a specific activity of 300 U/mg.

(3) Refinement

The precipitate from the trichloroacetic acid precipitation is dissolved with 500 ml of 0.1 M acetate buffer pH 6.0 and 0.3 volume of acetone is added at 0° C. The precipitate that forms is removed by centrifugation and again dissolved with 0.1 M acetate buffer, pH 6.0. Ammonium sulfate is added to the enzyme solution thus obtained to a molarity of 1.0. The precipitate is removed by centrifugation. Its specific activity amounts to about 800 U/mg.

The precipitate is again dissolved in the same buffer as in the ammonium sulfate fractionation, dialyzed against the same buffer, and then treated with DEAE Sephadex (balanced against the same buffer) and stirred for one hour. Then the exchange resin is washed with the same buffer and fractionally eluted with 0.2 M acetate buffer, pH 6.0. The active fractions are combined. The specific activity of the product thus obtained is between 2500 and 8000 U/mg in the individual fractions.

EXAMPLE 2

Determinaton of Glycerin by Hydrogen Peroxide Formation

Two reagents are prepared:
Reagent 1:
  0.1 mol/l triethanolamine/HCL buffer, pH 8.0
  3.6 mmol/l and 2 g/l isotridecyl ether
  4.7 mmol/l and 2 g/l sodium cholate
  10 mmol/l p-chlorophenol
  0.5 mmol/l aminosubstituted 4-aminoantipyrine
  10 U/ml peroxidase.
Reagent 2:
  500 U/ml glycerinoxidase.

For the performance of the determination, 2 ml of reagent 1 and 0.2 ml of reagent 2 are pipetted into a cell. The extinction $E_1$ is read on the photometer at 546 nm. Then the reaction is started by the addition of 20 microliters of sample. For the determination of free glycerin, all kinds of aqueous media can be used, such as food extracts, body fluids, and especially serum, as the sample; they can be used for the determination of triglycerides after saponification.

After 20 minutes of reaction, the extinction $E_2$ is read. The incubation temperature is 25° C.

Figure 2:
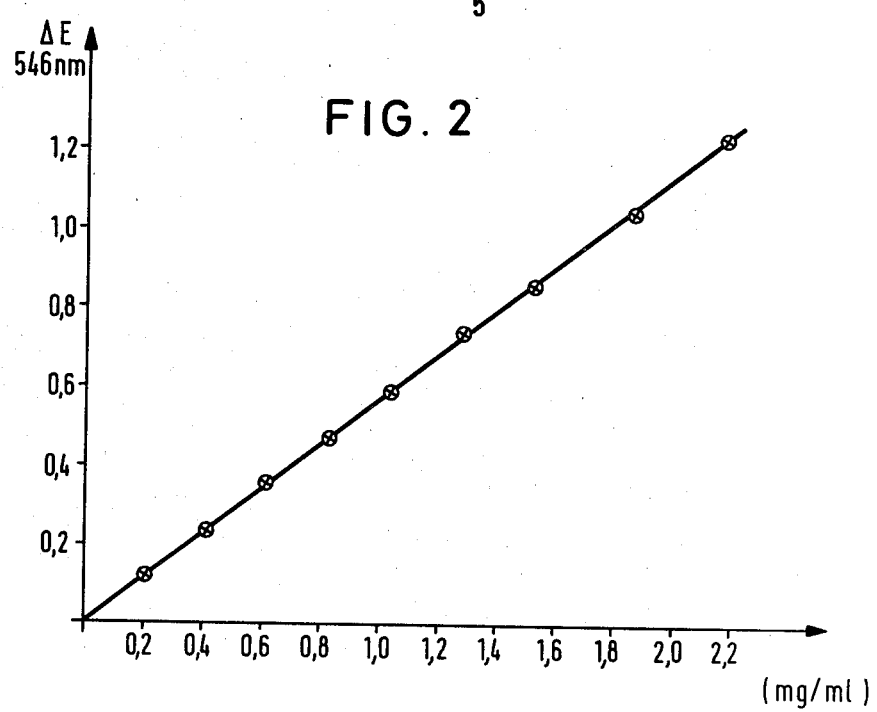

Evaluation is performed over a straight calibration line at which the measured extinction difference $$\Delta E = E_2 - E_1$$

of a glycerin standard solution is related to the glycerin or triglyceride concentration (FIG. 2 of the drawing).

The concentrations in the test mixture are:
0.09 mol/l triethanolamine/HCl buffer, pH 8.0
1.8 g/l (3.2 mmol/l) isotridecylether
4.3 mmol/l sodium cholate
9 mmol/l p-chlorophenol
0.45 mmol/l amino-substituted 4-aminoantipyrin
9 U/ml peroxidase
45 U/ml glycerinoxidase

EXAMPLE 3

Determination of Glycerin on the Basis of Oxygen Consumption

The apparatus represented in FIG. 1 of the drawing is used. The apparatus consists of a reaction vessel 1 in the form of a cylindrical chamber of transparent plastic having an inside diameter of 143 mm and an inside height of 220 mm. The chamber contains 1.8 ml of a solution of 18 mM of potassium iodide, 7.5 mM of ammonium heptamolybdate, 800 mM of sodium chloride and 50 U of glycerinoxidase in 0.2 M potassium phosphate buffer, pH 6.8. Into the reaction vessel extends the detector 3 which consists of an oxygen-sensitive electrode (WTW: OXI-Elektrode E 016). The detector is connected to the analyzer 4 (WTW: DIGI 610 Digital meter with OXI 610 D insert). At the bottom of the reaction vessel 1 is a magnetic stirrer 5.

20 microliters of an aqueous solution containing glycerin is put in through the opening 6 as the sample. The decrease of the oxygen concentration of the solution is measured during vigorous stirring with the magnetic stirrer. The observed oxygen consumption is recorded against the glycerin concentration.

EXAMPLE 4

Kinetic Determination

Samples:
aqueous standards (glycerin content from 10 to 100 mg/dl)
Reagent:
0.1 mol/l Pipes buffer, 1.7 mol/l H$_3$BO$_3$, PH=7.0
3.0 g/l isotridecyl ether
3.0 g/l sodium cholate
0.5 mmol/l 4aminoantipyrin, aminosubstituted
10.0 mmol/l p-chlorophenol
10.0 KU/l peroxidase
121.0 KU/l glycerinoxidase
Performance on the Gemsaec automatic Fast Analyzer:
Temperature: 25° C.
Measuring wavelength: 546 nm
Sample volume: 10 microliters
Diluent (H$_2$O): 50 microliters
Reagent volume: 500 microliters Measuring time: 1st reading: 35 sec. after start, 2nd reading: 315 sec. after start.
The following results were obtained:
Samples: aqueous standards

| Glycerin (UV test) (mg/dl) | % Recovered (Glyc-OD, according to invention) |
|---|---|
| 11 | 105 |
| 21 | 101 |
| 32 | 100 |
| 43 | 101 |
| 54 | 100 |
| 65 | 99 |
| 76 | 99 |
| 87 | 99 |
| 96 | 102 |

It is preferable in the case of kinetic determination to use the following quantity ratios in the reagent:

0.05 to 0.5 mol/l Pipes buffer, 0.5 to 2.0 mol/l $H_3BO_3$, pH 6.8 to 8.0
1 to 5 g/l isotridecyl ether
1 to 5 g/l sodium cholate
0.2 to 5 mmol/l 4-aminoantipyrin, aminosubstituted
5 to 50 mmol/l p-chlorophenol
5 to 50 KU/l peroxidase
100 to 250 KU/l glycerinoxidase The example shows that the invention can be performed with the very important automatic analyzers on hand in any clinical laboratory where analyses are routinely performed.

We claim:

1. Method for the determination of glycerin by oxidation with oxygen in the presence of glycerinoxidase and measurement of the oxygen consumption or of the formation of $H_2O_2$, characterized in that a glycerinoxidase from Aspergillus spec. DSM 1729 is used.

2. Method of claim 1, characterized in that the oxygen consumption is measured polarimetrically.

3. Method of claim 1, characterized in that the formed $H_2O_2$ is determined enzymatically with catalase or peroxidase.

4. Reagent for the determination of glycerin, characterized in that it consists of glycerinoxidase from Aspergillus spec. DSM 1729 and a system for the determination of $H_2O_2$.

5. Reagent of claim 4, characterized in that it additionally contains an agent for the saponification of esterified glycerin.

6. Reagent of claim 4 or 5, characterized in that the system for the determination of $H_2O_2$ consists of catalase, acetylacetone, methanol and buffer.

7. Reagent of claim 4 or 5, characterized in that the system for the determination of $H_2O_2$ consists of peroxidase, at least one chromogen and buffer.

8. Reagent of claim 7, characterized in that it contains 2 to 150 U/ml glycerinoxidase, 0.5 to 100 U/ml peroxidase, 0.05 to 20 mmol/l chromogen and buffer, pH 6 to 9.

9. Reagent of claim 7, characterized in that it contains 100 to 250 KU/l glycerinoxidase, 5 to 50 KU/l peroxidase, 0.2 to 5 mmol/l chromogen and buffer, pH 6.8 to 8.0.

10. Reagent of claim 4, characterized in that it is impregnated in a support material such as paper.

11. Method of producing glycerinoxidase from Aspergillus spec. DSM 1729, characterized in that Aspergillus spec. DSM 1729 is cultured in a suitable nutrient medium and the glycerinoxidase is obtained from the cell mass or from the culture medium.

12. Method of claim 11, characterized in that a medium is used which contains 20 to 200 g/l glycerin, 5 to 100 g/l malt extract, 0.5 to 5 g/l yeast extract, 0.2 to 5 g/l dipotassium phosphate, 0.2 to 5 g/l potassium nitrate, 0.1 to 5 g/l calcium carbonate, 0.1 to 1 g/l sodium chloride, 0.001 to 0.1 g/l ferrosulfate (measured as heptahydrate), 0.1 to 5 g/l magnesium sulfate (measured as heptahydrate).

13. Method of claim 11 or 12, characterized in that the cell mass is disintegrated, separated from the insoluble, and the glycerinoxidase is precipitated from the supernatant fluid with trichloroacetic acid.

14. Method of claim 13, characterized in that the precipitation is performed at pH 4.6 to 5.4.

15. Method of claim 13, characterized in that an acetone precipitation, an ammonium sulfate fractionation and an adsorption on a weakly basic ion exchanger are then performed.

16. Glycerinoxidase from Aspergillus spec. DSM 1729 having a molecular weight of about 90000, a specific activity of 2000 to 8000 U/mg, which is inhibited by SH reagents and not inhibited by copper sulfate and lead acetate.

* * * * *